United States Patent [19]

Morgan

[11] Patent Number: 4,658,013

[45] Date of Patent: Apr. 14, 1987

[54] ANALGESIC AND/OR OPIATE ANTAGONIST TRIPEPTIDE AMIDES AND PROCESSES FOR PREPARATION AND COMPOSITIONS THEREOF

[75] Inventor: Barry A. Morgan, Albany, N.Y.

[73] Assignee: Sterling Drug Inc., New York, N.Y.

[21] Appl. No.: 468,678

[22] Filed: Feb. 22, 1983

Related U.S. Application Data

[63] Continuation-in-part of Ser. No. 287,865, Jul. 28, 1981, abandoned.

[51] Int. Cl.$^4$ .......................... C07K 7/12; C07K 5/08; A61K 37/24
[52] U.S. Cl. .................................... 530/302; 530/331; 514/807
[58] Field of Search ................. 260/112.5 E; 530/302, 530/331; 514/807

[56] References Cited

U.S. PATENT DOCUMENTS

| | | | |
|---|---|---|---|
| 4,127,534 | 11/1978 | Coy et al. ............................... | 260/8 |
| 4,178,371 | 12/1979 | Morgan ........................ | 260/112.5 E |
| 4,254,023 | 3/1981 | Stewart et al. ................ | 260/112.5 E |
| 4,254,024 | 3/1981 | Stewart et al. ................ | 260/112.5 E |
| 4,261,883 | 4/1981 | Smolarsky .................... | 260/112.5 R |
| 4,350,627 | 9/1982 | de Castigliane et al. ..... | 260/112.5 E |

OTHER PUBLICATIONS

Vavrek et al., Abstracts of International Narcotics Research Conference, Jul. 26-30, 1981, Kyoto, Japan, Abstract P-76.

*Primary Examiner*—Delbert R. Phillips
*Attorney, Agent, or Firm*—Theodore C. Miller; Paul E. Dupont; B. Woodrow Wyatt

[57] ABSTRACT

A genus of tripeptide amides and fifteen species thereof of Examples 4-18, which are useful as analgesics and/or opiate antagonists, three processes for preparation thereof, pharmaceutical compositions thereof, and the three tripeptide amide species of Examples 1-3, which are not within the genus and are useful as analgesics and/or opiate antagonists, are disclosed.

1 Claim, No Drawings

ANALGESIC AND/OR OPIATE ANTAGONIST TRIPEPTIDE AMIDES AND PROCESSES FOR PREPARATION AND COMPOSITIONS THEREOF

CROSS-REFERENCE TO RELATED APPLICATION

This application is a continuation-in-part of my copending application Ser. No. 287,865 filed July 28, 1981 and now abandoned.

BACKGROUND OF THE INVENTION

1. Field of the Invention

The invention relates to tripeptide amides which are useful as analgesics and/or opiate antagonists.

2. Description of the Prior Art

Coy et al. U.S. Pat. No. 4,127,534 describes a genus of tripeptides having the structural formula H-Tyr-X-Gly-Y wherein: X is a chiral residue of a D-amino acid selected from the group consisting of D-alanine, D-leucine, D-isoleucine, D-valine, D-phenylalanine, D-tyrosine, D-tryptophan, D-serine, D-threonine, D-methionine, D-glutamic acid, D-glutamine, D-aspartic acid, D-proline, D-asparagine, D-lysine, D-arginine and D-histidine; and Y is selected from the group consisting of hydroxy, amino, aminoloweralkyl, aminodiloweralkyl [the foregoing two terms are considered incorrect and intended to mean loweralkylamino and diloweralkylamino], or lower alkoxy; and the pharmaceutically acceptable salts thereof
which are stated to be "useful as analgesics, anti-depressants, tranquilizers, sedatives or hypnotics when administered to mammalian hosts". The genus most closely approaches the presently described and claimed invention when X is a chiral residue of D-alanine, D-phenylalanine, D-serine, D-threonine, D-methionine, D-glutamic acid, D-glutamine, D-aspartic acid, D-asparagine or D-lysine and Y is loweralkylamino or diloweralkylamino.

Smolarsky U.S. Pat. No. 4,261,883 describes a genus of tripeptide and tetrapeptide amides having the structural formula

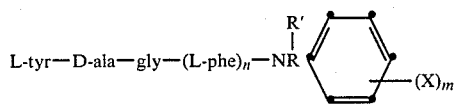

wherein:
R is alkylene of from two to three carbon atoms, preferably polymethylene, or 2-propenylene-1,3;
R' is hydrogen or alkyl of from 1 to 6, usually 1 to 4, more usually 1 to 2 carbon atoms, i.e. methyl and ethyl;
X is an electron withdrawing or an electron donating group, usually of from 1 to 20, more usually of from 1 to 12 atoms other than hydrogen, which are carbon, oxygen, nitrogen or sulfur, usually carbon, oxygen and nitrogen, which is substituted on the phenyl, and may be amino, alkylamino or dialkylamino, wherein the alkyl groups are of from one to three carbon atoms; azido, nitro, cyano, halo of atomic number 9 to 53, more usually of atomic number 9 to 35; nonoxo-carbonyl of from 1 to 18, usually 1 to 12, more usually 1 to 4 carbon atoms, including amides and esters, as well as the parent acid; acyl groups of from 1 to 4, usually 1 to 2 carbon atoms; e.g. formyl and acetyl; oxy, including hydroxy and alkoxy of from 1 to 18, usually 1 to 12, more usually 1 to 3 carbon atoms, frequently of from 1 to 2 carbon atoms; thio, including mercapto and alkylthio of the same limitations as alkoxy; alkyl of from 1 to 18, usually 1 to 12, more usually 1 to 3, frequently 1 to 2 carbon atoms; where there is more than one substituent, the substituents may be the same or different;
m is zero to two, usually zero to one; and
n is zero to one, usually one.
which are stated to "provide a wide range of physiological effects, such as mood altering effects, analgesia, muscle relaxation, and blood flow regulation". The genus most closely approaches the presently described and claimed invention when R is alkylene of from two to three carbon atoms, R' is hydrogen or alkyl of 1 to 5 carbon atoms, X is methyl, fluoro, chloro or methoxy, m is one and n is zero.

Even at closest approach the C-terminal amino acid of both the Coy et al. and Smolarsky genuses is glycyl and thus still differs significantly from that of the presently described and claimed invention.

Vavrek et al. (Abstracts of International Narcotics Research Conference, July 26–30, 1981, Kyoto, Japan, Abstract P-76) describes "Tyr-D-Ala-Phe-NH$_2$" as possessing "25% of the activity of Met-enkephalin" "on the stimulated guinea pig ileum". At closest approach the generic aspect of the presently described and claimed invention differs from the Vavrek et al. tripeptide amide in the amino acid moiety corresponding to Phe, wherein phenyl is separated from the α-carbon atom by from two to five methylenes instead of by one. A significant difference in biological properties results. HTyrDAlaHfeNH$_2$ (Example 9) of the presently described and claimed invention, which differs from the Vavrek et al. tripeptide amide by only one methylene, showed a potency of 120% of Met$^5$-enkephalin in the guinea pig ileum test, thus almost fivefold greater than that reported for the Vavrek et al. tripeptide amide.

In three tripeptide amide species which are not within the generic aspect thereof the presently described and claimed invention differs from the Vavrek et al. tripeptide amide by having one or two substituents on the amide nitrogen atom and/or a different amino acid moiety than D-Ala.

SUMMARY OF THE INVENTION

In a composition of matter aspect the invention is L-2-[D-2-(L-N$^2$-R$_1$-N-R$_2$-tyrosinamido)-2-R$_3$-2-R$_4$-N-R$_5$-acetamido]-2-R$_6$-N-R$_7$-N-R$_8$-acetamide having the structural formula

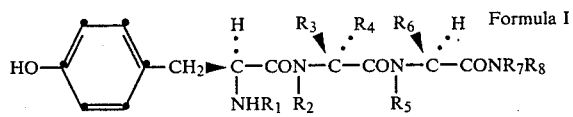

wherein
R$_1$ is hydrogen, methyl, ethyl, propyl or isopropyl;
R$_2$ is hydrogen or alkyl of one to five carbon atoms;
R$_3$ is hydrogen or methyl;
R$_4$ is alkyl of one to five carbon atoms; or wherein the

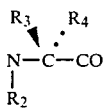

moiety is D-seryl, D-threonyl, D-phenylalanyl, 3-amino-D-alanyl, 3-dimethylamino-D-alanyl, D-2,4-diaminobutyryl, D-glutamyl, D-glutaminyl, D-methionyl, D-S-oxomethionyl, D-S-dioxomethionyl or L-prolyl;

$R_5$ is hydrogen or alkyl of one to five carbon atoms;
$R_6$ is $(CH_2)_mAr$, wherein m is an integer from 2 through 5 and
  Ar is phenyl or phenyl substituted by methyl, fluoro, chloro or methoxy;
$R_7$ is hydrogen, alkyl of one to five carbon atoms or $(CH_2)_mAr$
  wherein m is an integer from 1 through 5 and Ar is phenyl or phenyl substituted by methyl, fluoro, chloro or methoxy; and
$R_8$ is hydrogen, alkyl of one to five carbon atoms or $(CH_2)_nX$
  wherein n is an integer from 2 through 5 and X is hydroxy, amino, methylamino, dimethylamino, dimethyloxoamino, mercapto, methylmercapto, methylsulfinyl, methylsulfonyl, carboxy, carbamoyl, methylcarbamoyl or dimethylcarbamoyl;

or a pharmaceutically acceptable acid addition salt thereof.

The compounds of Formula I are useful as analgesics and/or opiate antagonists.

In a first process aspect the invention is the process of preparing L-2-[D-2-(L-$N^2$-$R_1$-N-$R_2$-tyrosinamido)-2-$R_3$-2-$R_4$-N-$R_5$-acetamido]-2-$R_6$-N-$R_7$-N-$R_8$-acetamide of Formula I which comprises condensing a suitably carboxyl-activated derivative of D-2-(L-$N^2$-$R_1$-N-$R_2$-tyrosinamido)-2-$R_3$-2-$R_4$-acetic acid with L-2-$R_5$NH-2-$R_6$-N-$R_7$-N-$R_8$-acetamide, concomitantly protecting and deprotecting the N-terminal α-amino and tyrosyl phenolic hydroxyl groups as required.

In a second process aspect the invention is the process of preparing L-2-[D-2-(L-$N^2$-$R_1$-N-$R_2$-tyrosinamido)-2-$R_3$-2-$R_4$-N-$R_5$-acetamido]-2-$R_6$-N-$R_7$-N-$R_8$-acetamide of Formula I which comprises condensing a suitably carboxyl-activated derivative of L-N-$R_1$-tyrosine with L-2-(D-$R_2$NH-2-$R_3$-2-$R_4$-N-$R_5$-acetamido)-2-$R_6$-N-$R_7$-N-$R_8$-acetamide, concomitantly protecting and deprotecting the N-terminal α-amino and tyrosyl phenolic hydroxyl groups as required.

In a third process aspect the invention is the process of preparing L-2-[D-2-(L-$N^2$-$R_1$-N-$R_2$-tyrosinamido)-2-$R_3$-2-$R_4$-N-$R_5$-acetamido]-2-$R_6$-N-$R_7$-N-$R_8$-acetamide of Formula I which comprises condensing a suitably carboxyl-activated derivative of L-2-[D-2-(L-$N^2$-$R_1$-N-$R_2$-tyrosinamido)-2-$R_3$-2-$R_4$-N-$R_5$-acetamido]-2-$R_6$-acetic acid with $HNR_7R_8$, concomitantly protecting the N-terminal α-amino and tyrosyl phenolic hydroxyl groups as required.

In another composition of matter aspect the invention is a pharmaceutical composition for use as an analgesic and/or opiate antagonist consisting essentially of an analgesically and/or opiate antagonistically effective concentration of L-2-[D-2-(L-$N^2$-$R_1$-N-$R_2$-tyrosinamido)-2-$R_3$-2-$R_4$-N-$R_5$-acetamido]-2-$R_6$-N-$R_7$-N-$R_8$-acetamide of Formula I or a pharmaceutically acceptable acid addition salt thereof and a pharmaceutically acceptable vehicle.

When $R_2$, $R_4$, $R_5$, $R_7$ and $R_8$ of Formula I is alkyl of one to five carbon atoms it can be any of the possible primary, secondary and tertiary alkyls of one to five carbon atoms, especially including methyl, ethyl, n-propyl, isopropyl, n-butyl, t-butyl, n-pentyl and 3-methylbutyl.

In a preferred subgeneric composition of matter aspect the invention is a compound of Formula I wherein the

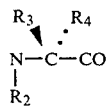

moiety is D-alanyl, D-methionyl, D-S-oxomethionyl or D-S-dioxomethionyl and wherein $R_5$ is hydrogen or methyl and $R_6$ is $(CH_2)_mAr$ wherein m is 2 or 3 and Ar is phenyl.

In a further preferred composition of matter aspect the invention is three tripeptide amide species not within the genus of Formula I and having the following structural formulas, which represent the free base forms of the compounds of Example 1-3 whose preparation and biological properties are described below.

| Structural Formula | Example |
|---|---|
| HTyrD-AlaPheNHCH$_2$CH$_2$CHMe$_2$ | 1 |
| HTyrD-AlaPheNCH$_2$CH$_2$CHMe$_2$<br>    |<br>    CH$_2$CH$_2$Ph | 2 |
| HTyrD-DaaPheNHCH$_2$CH$_2$CHMe$_2$ | 3 |

These three species are also useful as analgesics and/or opiate antagonists.

In a most preferred composition of matter aspect the invention is certain species of the above-described preferred subgenus of Formula I and having the following structural formulas, which represent the free base forms of the compounds of Examples 4–18 whose preparations and biological properties are described below.

| Structural Formula | Example |
|---|---|
| HTyrD-AlaHfeNHCH$_2$CH$_2$CHMe$_2$ | 4 |
| HTyrMeD-AlaHfeNHCH$_2$CH$_2$CHMe$_2$ | 5 |
| MeTyrD-AlaHfeNHCH$_2$CH$_2$CHMe$_2$ | 6 |
| HTyrD-AlaHhfNHCH$_2$CH$_2$CHMe$_2$ | 7 |
| HTyrD-AlaHfeNCH$_2$CH$_2$CHMe$_2$<br>    |<br>    Me | 8 |
| HTyrD-AlaHfeNH$_2$ | 9 |
| MeTyrD-AlaHfeNH$_2$ | 10 |
| HTyrD-AlaHfeNHMe | 11 |
| HTyrD-AlaMeHfeNHCH$_2$CH$_2$CHMe$_2$ | 12 |
| MeTyrD-AlaHfeNHMe | 13 |
| HTyrD-AlaHfeNHCH$_2$CH$_2$NMe$_2$ | 14 |
| HTyrD-MetHfeNHCH$_2$CH$_2$CHMe$_2$ | 15 |
| HTyrD-Met(O)HfeNHCH$_2$CH$_2$CHMe$_2$ | 16 |
| HTyrD-Met(O$_2$)HfeNHCH$_2$CH$_2$CHMe$_2$ | 17 |
| HTyrD-AlaHfeNHCH$_2$CH$_2$Ph | 18 |

In the foregoing structural formulas of species of the invention

Tyr represents L-tyrosyl,
D-Ala represents D-alanyl,
Phe represents L-phenylalnyl,
Me represents methyl,
Ph represents phenyl,
D-Daa represents 3-dimethylamino-D-alanyl,
Hfe represents L-2-amino-4-phenylbutanoyl,
Hhf represents L-2-amino-5-phenylpentanoyl,
D-Met represents D-methionyl,
D-Met(O) represents D-S-oxomethionyl, and
D-Met(O$_2$) represents D-S-dioxomethionyl.

The symbols for the amino acid moieties do not include the N-terminal and C-terminal groups.

DETAILED DESCRIPTION OF THE INVENTION INCLUSIVE OF THE PREFERRED EMBODIMENTS

Preparation of the Compounds

The protection, activation, condensation and deprotection steps required to prepare the compounds of Formula I are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid, dipeptide and tripeptide intermediates can be formed and used with or without being isolated and include the acyl halides and pseudohalides, especially the acyl azides; the anhydrides, especially the mixed anhydrides and most especially the mixed anhydride with diphenylphosphinyl chloride, isobutyl chloroformate or pivalyl chloride; derivatives formed by addition reactions, especially using dicyclohexylcarbodiimide; displaceable aryl derivatives of heterocyclic nitrogen; ring-openable activated heterocyclic systems; acylphosphonium derivatives; activated esters, especially 1-hydroxybenzotriazole, N-hydroxysuccinimide, nitrophenyl and pentafluorophenyl esters; and polymeric (solid phase) derivatives.

It is necessary that the N-terminal α-amino function be protected during the peptide and amide forming steps. It is preferred but not essential that the tyrosyl phenolic hydroxyl also be protected. The preferred α-amino protecting groups are benzyloxycarbonyl (Z), which can be removed by catalytic hydrogenation using palladium as catalyst or by hydrogen bromide in acetic acid, and t-butoxycarbonyl (Boc), which can be removed by acidic cleavage, for example, with hydrogen chloride in a suitable solvent or trifluoroacetic acid. Benzyl (Bz) and t-butyl (tBu) are the preferred tyrosyl phenolic hydroxyl protecting groups. Benzyl can be removed by catalytic hydrogenation using palladium as catalyst or by hydrogen bromide in acetic acid. t-Butyl can be removed by acidic cleavage, for example, with hydrogen chloride in a suitable solvent or trifluoroacetic acid.

The C-terminal carboxyl group, which must be protected during the peptide forming steps, can be protected as the carboxylate salt, the t-butyl ester, which can be removed by acidic cleavage, for example, with hydrogen chloride in a suitable solvent or trifluoroacetic acid, or the benzyl ester, which can be removed by catalytic hydrogenation using palladium as catalyst. In the first and second process aspects of the invention it is protected as the amide, which is, of course, not removed.

The synthetic intermediates necessary to carry out the process aspects of the invention are known classes of compounds and are commercially available or can be made by methods specifically or generally described in the chemical literature.

Besides being preparable by the three process aspects of the invention the compounds of Formula I wherein the

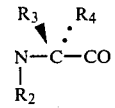

moiety is D-S-oxomethionyl or D-S-dioxomethionyl can also be prepared by oxidation by known methods of the respective corresponding compounds of Formula I wherein the same moiety is D-methionyl.

The acid addition salts of the compounds of Formula I are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of Formula I and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophylization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GLC), column chromatography, high pressure liquid chromatography (HPLC), thin layer chromatography (TLC) and/or amino acid analysis.

EXAMPLE 1

HTyrD-AlaPheNHCH$_2$CH$_2$Me$_2$

A. ZTyr(Bz)D-AlaOMe

Triethylamine (5.7 ml.), then isobutylchloroformate (5.3 ml.), were added with stirring to a solution of N-benzyloxycarbonyl-O-benzyl-L-tyrosine (16.68 g.) in acetone (175 ml.) maintained at −20° C. The solution was stirred for 10 minutes at −20° C., then D-alanine methyl ester hydrochloride (6.4 g.) and triethylamine (5.7 ml.) in chloroform (65 ml.) were added. Stirring was continued one hour at this temperature, then four hours at room temperature. The mixture was filtered and the filtrate was stripped of volatiles. The residue and the filtration solid were combined and distributed between water (200 ml.) and ethyl acetate (250 ml.). Part of the product was collected by filtration and washed with aqueous hydrochloric acid, water, saturated sodium bicarbonate and water. The ethyl acetate layer was washed with cold aqueous hydrochloric acid (0.5N), water, saturated aqueous sodium bicarbonate, water again and saturated aqueous sodium chloride and stripping of volatiles, yielding another part of the product. The two parts were combined and recrystallized from absolute ethanol, affording (N-benzyloxycarbonyl-O-benzyl-L-tyrosyl)-D-alanine methyl ester (15.28 g.; m.r. 161°–163° C.; $[\alpha]_D^{25} -11.7°$, c=2, dimethylformamide).

B. ZTyr(OBz)D-AlaNHNH$_2$

A solution of hydrazine hydrate (5.05 ml.) in ethanol (45 ml.) was added to a solution of (N-benzyloxycarbonyl-O-benzyl-L-tyrosyl)-D-alanine methyl ester (15.18 g.) in tetrahydrofuran (135 ml.). The resulting solution was stirred at room temperature and seeded. (N-Benzyloxycarbonyl-O-benzyl-L-tyrosyl)-D-alanyl hydrazide (13.2 g.; m.r. 216°–218° C.; $[\alpha]_D^{25} -21.4°$, c=2, dimethylformamide) separated from the solution as a crystalline solid.

C. ZPheNHCH$_2$CH$_2$CHMe$_2$

Diisopropylethylamine (5.2 ml.), then diphenylphosphinyl chloride (7.1 g.), were added with cooling at −20° C. and stirring to a solution of N-benzyloxycarbonyl-L-phenylalanine (9 g.) in tetrahydrofuran (80 ml.) and stirring was continued for 10 minutes. 3-Methylbutylamine (isoamylamine, 3.6 ml., 2.7 g.) was added. The mixture was stirred one hour at 0° C., then two hours at room temperature, then stripped of volatiles. The residue was distributed between ethyl acetate and water. The ethyl acetate layer was washed twice with aqueous citric acid (5%), water, saturated aqueous sodium bicarbonate, water again and saturated aqueous sodium chloride, dried over magnesium sulfate and stripped of ethyl acetate. Recrystallization of the residue from isopropyl acetate-hexane afforded N$^2$-benzyloxycarbonyl-N-(3-methylbutyl)-L-phenylalaninamide as white needles in two crops (3.77 g., m.r. 123°–126° C.; 3.40 g., m.r. 119°–126° C.).

D. HPheNHCH$_2$CH$_2$CHMe$_2$

A mixture of N$^2$-benzyloxycarbonyl-N-(3-methylbutyl)-L-phenylalaninamide (7.0 g.), ethanol (200 ml.) and palladium on carbon (10%, 250 mg.) was hydrogenated under pressure (40 p.s.i.g.) for three hours (10% uptake). Concentrated hydrochloric acid (1.65 ml.) was added and the hydrogenation was continued overnight. The mixture was filtered, and the filtrate was stripped of volatiles. A small amount of crystals separated from an ether-ethanol solution of the residue. The mother liquor was stripped of volatiles and purified by reverse phase high pressure liquid chromatography on octadecylsilated silica gel using ammonium acetate (0.2%) in methanol-water (65:35) as the eluant, affording N-(3-methylbutyl)-L-phenylalaninamide (2.5 g.) as a clear gum.

E. ZTyr(Bz)D-AlaPheNHCH$_2$CH$_2$CHMe$_2$

Butyl nitrite (0.51 ml.), then hydrogen chloride in dimethylformamide (3.3N, 1.33 ml.), were added with stirring and cooling at ice-salt temperature to a solution of (N-benzyloxycarbonyl-O-benzyl-L-tyrosyl)-D-alanyl hydrazide was negative almost immediately. Diisopropylethylamine (1.52 ml.), then N-(3-methylbutyl)-L-phenylalaninamide (1.12 g.), were added, and the mixture was stirred at 0° C. for two hours, stored at about 5° C. over the weekend, then quenched in ice-water. The resulting mixture gave a suspension with ethyl acetate. The suspension was washed with water, aqueous citric acid (5%), water again, saturated aqueous sodium bicarbonate, water again, and saturated aqueous sodium chloride, and filtered, affording a white solid (about 4 g.). The filtrate was dried over magnesium sulfate and stripped of ethyl acetate. The residue and the white solid were combined and recrystallized from ethanol (90%, 125 ml.), affording (N-benzyloxycarbonyl-O-benzyl-L-tyrosyl)-D-alanyl-N-(3-methylbutyl)-L-phenylalaninamide (2.00 g., m.r. 194°–195° C. with resolidification and remelting at 205°–206° C.).

F. HTyrDAlaPheNHCH$_2$CH$_2$CHMe$_2$

A mixture of (N-benzyloxycarbonyl-O-benzyl-L-tyrosyl)-D-alanyl-N-(3-methylbutyl)-L-phenylalaninamide (1.95 g.), palladium on carbon (10%, 200 mg.) and acetic acid (100 ml.) was hydrogenated under pressure (30 p.s.i.g.) for six hours (uptake 60%), then without shaking overnight (uptake 100%), then filtered. The filtrate was stripped of volatiles. Reverse phase high pressure liquid chromatography of the residue on octadecylsilated silica gel (350 g.) using ammonium acetate (0.2%) in methanol-water (65:35) as the eluant (50–100 ml./min.) gave in fraction 4 at a k' value of 3.0 a product, which was passed through the column again. Elution was first with water to remove ammonium acetate and then with methanol to remove the product, which was converted into the phosphate salt on an ion exchange column as an aqueous methanol (1:2) solution. The solution was stripped of methanol. Water was added, and the solution was concentrated, filtered and lyophilized, affording as an amorphous white solid L-tyrosyl-D-alanyl-N-(3-methylbutyl)-L-phenylalaninamide phosphate salt (1:1) monohydrate (1.18 g.).

EXAMPLE 2

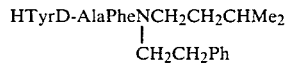

By the method of Example 1 and using (3-methylbutyl)-(2-phenylethyl)amine (prepared by diborane reduction of N-(3-methylbutyl)-2-phenylacetamide; m.r. of hydrochloride salt, 253°–257° C.) instead of 3-methylbutylamine, there was prepared as an amorphous white solid L-tyrosyl-D-alanyl-N-(3-methylbutyl)-N-(2-phenylethyl)-L-phenylalaninamide monohydrochloride sesquihydrate.

EXAMPLE 3

A. BocD-DaaOH

A mixture of 3-amino-N$^2$-(t-butoxycarbonyl)-D-alanine (8.0 g.), aqueous formaldehyde (35%, 116 ml.) and platinium dioxide (590 mg.) was hydrogenated under pressure. After one day more platinum dioxide (500 mg.) was added and the hydrogenation was continued. The mixture was filtered and the filtrate was stripped of volatiles. Purification of the residue by reverse phase high pressure liquid chromatography on octadecylsilated silica gel (350 g.) using water-methanol (92:8) as the eluant afforded 3-dimethyamino-N$^2$-(t-butoxycarbonyl)-D-alananine monhydrate (2.04 g.; $[\alpha]_D^{25} -20.7°$, c=1, dimethyformamide) as a colorless oil.

B. BocD-DaaPheNHCH₂CH₂CHMe₂

By the method of part A of Example 1, in two runs, and using tetrahydrofuran instead of acetone as solvent 3-dimethylamino-N²-(t-butoxycarbonyl)-D-alanine monohydrate (1.00 g., 716 mg.) was condensed with N-(3-methylbutyl)-L-phenylalaninamide (part D of Example 1, 1.05 g., 760 mg.). The products (2.06 g., 1.21 g.) were combined and purified by reverse phase high pressure liquid chromatography on octadecylsilated silica gel using ammonium acetate (0.2%) in methanol-water (70:30) as the eluant, affording [3-dimethylamino-N²-(t-butoxycarbonyl)-D-alanyl]-N-(3-methylbutyl)-L-phenylalaninamide as an oil (1.96 g.).

C. HD-DaaPheNHCH₂CH₂CHMe₂

A solution of [3-dimethylamino-N²-(t-butoxycarbonyl)-D-alanyl]-N-(3-methylbutyl)-L-phenylalaninamide (1.84 g.) in acetic acid saturated with hydrogen chloride (50 ml.) was stirred for one and one half hours at room temperature, then stripped of volatiles under vacuum. A solution of the residue (1.87 g.) in ethyl acetate was washed with saturated aqueous sodium bicarbonate, then saturated aqueous sodium chloride, and filtered. Hydrogen chloride (8.2 millimoles) in ethanol was added and the solution was stripped of volatiles, affording (3-dimethylamino-D-alanyl)-N-(3-methylbutyl)-L-phenylalaninamide dihydrochloride as a gum.

D. ZTyr(Bz)D-DaaPheNHCH₂CH₂CHMe₂

A solution of (3-dimethylamino-D-alanyl)-N-(3-methylbutyl)-L-phenylalaninamide dihydrochloride (4.1 millimoles), triethylamine (1.14 ml., 8.2 millimoles) and N-benzyloxycarbonyl-O-benzyl-L-tyrosine pentafluorophenyl ester (2.34 g., 4.1 millimoles) in tetrahydrofuran (25 ml.) was stirred for two hours, then allowed to stand overnight, at room temperature, then stripped of volatiles. A solution of the residue in ethyl acetate was washed three times with saturated aqueous sodium bicarbonate and once with saturated aqueous sodium chloride, dried over magnesium sulfate, filtered and stripped of ethyl acetate. Recrystallization of the crystalline residue from ethyl acetate-hexane afforded (N-benzyoxycarbonyl-O-benzyl-L-tyrosyl)-(3-dimethylamino-D-alanyl)-N-(3-methylbutyl)-L-phenylalaninamide (2.03 g.).

E. HTyrD-DaaPheNHCH₂CH₂CHMe₂

A mixture of (N-benzyloxycarbonyl-O-benzyl-L-tyrosyl)-(3-dimethylamino-D-alanyl)-N-(3-methylbutyl)-L-phenylalaninamide (1.94 g.), palladium on carbon (10%, 200 mg.) and acetic acid (40 ml.) was hydrogenated under pressure overnight, then filtered. The filtrate was stripped of volatiles. Separation of the resulting mixture by reverse phase high pressure liquid chromatography on octadecylsilated silica gel using ammonium acetate (0.15%) in methanol-water (60:40) as the eluant was unsuccessfully attempted. Separation was achieved by normal phase column chromatgraphy on silica gel using chloroform-methanol-acetic acid-water (40:8:1:1) as the eluant. An aqueous solution of the oily product (1.1 g.) was filtered and lyophilized, affording as an amorphous white solid L-tyrosyl-3-(dimethylamino)-D-alanyl-N-(3-methylbutyl)-L-phenylalaninamide diacetate salt.

EXAMPLE 4

HTyrD-AlaHfeNHCH₂CH₂CHMe₂

A. BocHfeNHCH₂CH₂CHMe₂

A solution of S(+)-2-aminobenzenebutanoic acid (5 g.) and di-t-butyldicarbonate (7.92 g.)in dioxane (25 ml.) and aqueous sodium hydroxide (1N, 10 ml.) was stirred for one hour at room temperature while maintaining the pH at 8.00. More di-t-butyldicarbonate (1 g.) was added and stirring was continued at pH 8.00. Water and ether were added and the pH was adjusted to 9. The aqueous layer was washed with ether, adjusted to pH 2.0 with potassium hydrogen sulfate, and extracted with ethyl acetate. The ethyl acetate layer was dried over magnesium sulfate and stripped of solvent, affording as a pale yellow gum S-2-(t-butoxycarbonylamino)benzenebutanoic acid (8.2 g.), whose dicyclohexylamine salt (10.87 g., m.r. 148°-153° C.) was prepared from a solution of the gum and the amine (5.6 ml.) in ether (70 ml.).

The free acid was liberated by extracting a solution of the dicyclohexylamine salt in ethyl acetate (200 ml.) with aqueous citric acid (5%, once with 200 ml., twice with smaller amounts), then with water, then with saturated aqueous sodium chloride and drying the solution over magnesium sulfate and stripping it of solvent. Pentafluorophenol (4.41 g.), then dicyclohexylcarbodiimide (4.95 g.), were added to a solution of the resulting gum (about 7 g.) in ethyl acetate (50 ml.). The resulting mixture was stirred for three hours at 0° C., refrigerated overnight, filtered to remove dicyclohexylurea (5.07 g.), and stripped of solvent. Crystallization of the resulting yellow oil from hexane (about 100 ml.) afforded as white crystals the pentafluorophenyl ester of S-2-(t-butoxycarbonylamino)benzenebutanoic acid (8.60 g.; m.r. 94°-96° C.; $[\alpha]_D^{25}$ +9.8°, c=2, chloroform).

A solution of S-2-(t-butoxycarbonylamino)benzenebutanoic acid pentafluorophenyl ester (4.0 g.) and 3-methyl butylamine (isoamylamine, 1.16 ml.) in tetrahydrofuran (15 ml.) was stirred for three hours at room temperature, then partitioned between ether and water. The ether layer was washed twice with aqueous citric acid (5%), once with water and twice with saturated aqueous sodium bicarbonate, dried over magnesium sulfate and stripped of solvent. Purification of the yellow oil (4.4 g.) by high pressure liquid chromatography on silica gel (350 g.) using hexane-ethyl acetate (85:15) as the eluant afforded as a clear, colorless oil S-2-(t-butoxycarbonylamino)-N-(3-methylbutyl)benzenebutanamide (3.40 g.).

B. HHfeNHCH₂CH₂CHMe₂

A solution of S-2-(t-butoxycarbonylamino)-N-(3-methylbutyl)benzenebutanamide (3.2 g.) in ethyl acetate-hydrogen chloride (4N, 25 ml.) was stirred for two hours at room temperature, then stripped of volatiles, affording S-2-amino-N-(3-methylbutyl)benzenebutanamide hydrochloride.

C. ZTyr(Bz)D-AlaHfeNHCH₂CH₂CHMe₂

By the method of part E of Example 1 (N-benzyloxycarbonyl-O-benzyl-L-tyrosyl)-D-alanyl hydrazide (part B of Example 1, 1.47 g.) was condensed with S-2-amino-N-(3-methylbutyl)benzenebutanamide hydrochloride (1.00 g.) and the product was purified by boiling with ethanol (95%, 100 ml.), cooling and filtering, affording S-2-[(N-benzyloxycarbonyl-O-benzyl-L-tyrosyl)-D-alanyl]amino-N-(3-methylbutyl)benzenebutanamide (1.59 g.).

D. HTyrD-AlaHfeNHCH$_2$CH$_2$CHMe$_2$

By the method of part F of Example 1 S-2[(N-benzyloxycarbonyl-O-benzyl-L-tyrosyl)-D-alanyl]amino-N-(3-methylbutyl)benzenebutanamide (1.47 g.) was deprotected and purified. The product was lyophilized, first from dilute hydrochloric acid (0.1N) and then from water, affording as an amorphous white solid (2S)-N-(3-methylbutyl)-2-[(L-tyrosyl-D-alanyl)amino]benzenebutanamide monohydrochloride monohydrate (860 mg.), whose free base is the compound of Formula I wherein $R_1$, $R_2$, $R_3$, $R_5$ and $R_7$ are each hydrogen, $R_4$ is methyl, $R_6$ is $(CH_2)_m Ar$ wherein m is 2 and Ar is phenyl, and $R_8$ is 3-methylbutyl.

EXAMPLE 5

HTyrMeD-AlaHfeNHCH$_2$CH$_2$CHMe$_2$

A. ZMeD-AlaOMe

Methyl iodide (25 ml.), then sodium hydride (50% in oil, 7.2 g.), were added with stirring to a solution of N-benzyloxycarbonyl-D-alanine (11.16 g.) in tetrahydrofuran (125 ml.) and dimethylformamide (13 ml.). The mixture was then stirred under reflux for 24 hours. Water (100 ml.) was added, the pH was adjusted to 5.5 with hydrochloric acid and sodium bicarbonate, and the solvents were stripped. The residue was distributed between ether and aqueous citric acid (5%). The ether layer was washed successively with water, saturated aqueous sodium bicarbonate, water and saturated aqueous sodium chloride, then dried over sodium sulfate and stripped of ehter, affording N-benzyloxycarbonyl-N-methyl-D-alanine methyl ester as a red oil (14.5 g.), which still contained the oil from the sodium hydride-oil mixture. TLC (silica gel, 3:1 hexane-ethyl acetate) of the red oil showed a single spot ($R_f \sim 0.5$).

B. HMeD-AlaOMe

A mixture of the red oil from part A of this example and hydrogen bromide in acetic acid (32%, 50 ml.) was stirred at room temperature for two hours, then stripped of volatiles. The residue was distributed between ether and water (75 ml.), and the aqueous layer was washed twice more with ether, then stripped of volatiles. After an unsuccessful attempt to crystallize the residue from methanol-ether, the methanol and ether were removed, ethanol and toluene were added, and the mixture was stripped of volatiles again. Crystallization of the residue from methanol (about 20 ml.)-ether afforded N-methyl-D-alanine methyl ester hydrobromide as white needles (7.18 g.; m.r. 116°–118° C.; $[\alpha]_D^{25} +6.0°$, c=2, dimethylformamide).

C. ZTyr(Bz)MeD-AlaOMe

Diisopropylethylamine (1.29 g.), then diphenylphosphinic chloride (2.37 g.), were added to a solution of N-benzyloxycarbonyl-O-benzyl-L-tyrosine (4.05 g.) in tetrahydrofuran (30 ml.) maintained at $-20°$ C., and the mixture was stirred at that temperature for 10 minutes. A solution of N-methyl-D-alanine methyl ester hydrobromide (1.98 g.) in tetrahydrofuran (20 ml.) was then added, followed by diisopropylethylamine (1.29 g.). The mixture was stirred for two hours at 0° C., then overnight at room temperature, then filtered, stripped of volatiles and distributed between ethyl acetate and aqueous citric acid (5%). The ethyl acetate layer was washed with water, saturated aqueous sodium bicarbonate, water again and saturated aqueous sodium chloride, then dried over magnesium sulfate and concentrated to a yellow gum (about 6 g.). Purification of the yellow gum by high pressure liquid chromatography on silica gel (350 g.) using hexaneethyl acetate (7:3) as the eluant afforded (N-benzyloxycarbonyl-O-benzyl-L-tyrosyl)-N-methyl-D-alanine methyl ester as a clear gum (3.2 g.) containing about a one-sixth molar amount of ethyl acetate as shown by NMR spectral analysis.

D. ZTyr(Bz)MeD-AlaNHNH$_2$

A mixture of (N-benzyloxycarbonyl-O-benzyl-L-tyrosyl)-N-methyl-D-alanine methyl ester one-sixth ethyl acetate solvate (2.8 g.), hydrazine hydrate (1.8 ml.) and methanol (50 ml.) was stirred overnight at room temperature. More hydrazine hydrate (1.8 ml.) was added and stirring was continued for another day. The volatiles were stripped, and the residue was distributed between water and ethyl acetate. The ethyl acetate layer was washed with aqueous citric acid (5%), saturated aqueous sodium bicarbonate and saturated aqueous sodium chloride, dried over magnesium sulfate, and stripped of ethyl acetate, affording (N-benzyloxycarbonyl-O-benzyl-L-tyrosyl)-N$^2$-methyl-D-alanyl hydrazide as a foam (2.5 g.).

E. ZTyr(Bz)MeD-AlaHfeNHCH$_2$CH$_2$CHMe$_2$

By the method of part E of Example 1 (N-benzyloxycarbonyl-O-benzyl-L-tyrosyl)-N$^2$-methyl-D-alanyl hydrazide (1.38 g.) was condensed with S-2-amino-N-(3-methylbutyl)benzenebutanamide hydrochloride (part B of Example 4), and the product was purified by high pressure liquid chromatography on silica gel using hexane-ethyl acetate (1:1) as the eluant, affording S-2-[(N-benzyloxycarbonyl-O-benzyl-L-tyrosyl)-N$^2$-methyl-D-alanyl]amino-N-(3-methylbutyl)benzenebutanamide (1.37 g.).

F. HTyrMeD-AlaHfeNHCH$_2$CH$_2$CHMe$_2$

By the method of part F of Example 1 S-2-[(N-benzyloxycarbonyl-O-benzyl-L-tyrosyl)-N$^2$-methyl-D-alanyl]amino-N-(3-methylbutyl)benzenebutanamide (1.25 g.) was deprotected, purified and isolated, affording as an amorphous white solid (2S)-N-(3-methylbutyl)-2-[(L-tyrosyl-N-methyl-D-alanyl)amino]benzenebutanamide phosphate (3:2) salt monohydrate (256 mg.), whose free base is the compound of Formula I wherein $R_1$, $R_3$, $R_5$ and $R_7$ are each hydrogen, $R_2$ and $R_4$ are each methyl, $R_6$ is $(CH_2)_m Ar$ wherein m is 2 and Ar is phenyl, and $R_8$ is 3-methylbutyl.

EXAMPLE 6

MeTyrD-AlaHfeNHCH$_2$CH$_2$CHMe$_2$

A. BocD-AlaHfeNHCH$_2$CH$_2$CHMe$_2$

A solution of N-(t-butoxycarbonyl)-D-alanine pentafluorophenyl ester (570 mg.), S-2-amino-N-(3-methylbutyl)benzenebutanamide hydrochloride (part B of Example 4, 400 mg.) and diisopropylethylamine (243 μl.) in tetrahydrofuran (10 ml.) was stirred at room temperature. 3-Dimethylaminopropylamine (1 millimole) was added to destroy unchanged N-(t-butoxycarbonyl)-D-alanine pentafluorophenyl ester shown by TLC, and stirring was continued for two hours. The mixture was stripped of volatiles. A solution of the residue in ethyl acetate was washed twice with aqueous citric acid (5%), once with saturated aqueous sodium bicarbonate and once with saturated aqueous sodium chloride, dried over magnesium sulfate and stripped of solvent. Th residual yellow gum (700 mg.) crystallized and was recrystallized from hexane, affording S-2-[N-(t-butoxycarbonyl)-D-alanyl]amino-N-(3-methylbutyl)benzenebutanamide (330 mg., m.r. 84°–86° C.).

B. HD-AlaHfeNHCH$_2$CH$_2$CHMe$_2$

A solution of S-2-[N-(t-butoxycarbonyl)-D-alanyl]amino-N-(3-methylbutyl)benzenebutanamide in ethyl acetatehydrogen chloride (3.4N, 10 ml.) was stirred for one hour at room temperature, then stripped of volatiles, affording S-2-(D-alanylamino)-N-(3-methylbutyl)-benzenebutanamide hydrochloride (240 mg.).

C. BocMeTyr(tBu)D-AlaHfeNHCH$_2$CH$_2$CHMe$_2$

By the method of part C of Example 1 N-(t-butoxycarbonyl)-O-(t-butyl)-N-methyl-L-tyrosine (267 mg.) was condensed with S-2-(D-alanylamino)-N-(3-methylbutyl)benzenebutanamide hydrochloride (240 mg.) and the product was purified by high pressure liquid chromatography on silica gel using ethyl acetate-hexane (6:4) as the eluant, affording S-2-[N-(t-butoxycarbonyl)-O-(t-butyl)-N-methyl-L-tyrosyl-D-alanylamino]-N-(3-methylbutyl)benzenebutanamide as a pale yellow gum (273 mg.).

D. MeTyrD-AlaHfeNHCH$_2$CH$_2$CHMe$_2$

A solution of S-2-[N-(t-butoxycarbonyl)-O-(t-butyl)-N-methyl-L-tyrosyl-D-alanylamino]-N-(3-methylbutyl)benzenebutanamide (260 mg.) in dioxane-hydrogen chloride (3.9N, 5 ml.) was stirred for one hour at room temperature, then diluted with ether (50 ml.). A solution of the resulting solid in water (20 ml.) was filtered and lyophilized, affording as an amorphous white solid (2S)-N-(3-methylbutyl)-2-[(N-methyl-L-tyrosyl-D-alanyl)amino]benzenebutanamide monhydrochloride monohydrate (146 mg.), whose free base is the compound of Formula I wherein $R_1$ and $R_4$ are each methyl, $R_2$, $R_3$, $R_5$ and $R_7$ are each hydrogen, $R_6$ is $(CH_2)_mAr$ wherein m is 2 and Ar is phenyl, and $R_8$ is 3-methylbutyl.

EXAMPLE 7

HTyrD-AlaHhfNHCH$_2$CH$_2$CHMe$_2$

A. BocHhfOH

The pH of a solution of D,L-2-aminobenzenepentanoic acid (5 g.) in dioxane (25 ml.) was adjusted to 8.5 with 1N aqueous sodium hydroxide. A solution of di-t-butyl dicarbonate (7.36 g.) in dioxane (10 ml.) was then added with stirring and while maintaining the pH constant. The solution was allowed to stand overnight at room temperature, diluted with water (100 ml.), stripped fo dioxane, and washed with ether. The pH was adjusted to 3.5. The resulting oil was extracted into ethyl acetate. The ethyl acetate extract was dried over magnesium sulfate and stripped of ethyl acetate. The resulting oil crystallized and was recrystallized from hexane, affording D,L-2-(t-butoxycarbonylamino)benzenepentanoic acid (6.83 g., m.r. 98°–99° C.).

B. BocHhfNHCH$_2$CH$_2$CHMe$_2$

By the method of part C of Example 1 D,L-2-(t-butoxycarbonylamino)benzenepentanoic acid (1.47 g.) was condensed with 3-methylbutylamine (1.16 ml.) and the resulting crystalline product was recrystallized from isopropyl acetate-hexane, affording D,L-2-(t-butoxycarbonylamino)-N-(3-methylbutyl)benzenepentanamide in two crops (980 mg., m.r. 95°–97° C.; 580 mg., m.r. 94°–95° C.).

C. HHhfNHCH$_2$CH$_2$CHMe$_2$

A solution of D,L-2-(t-butoxycarbonylamino)-N-(3-methylbutyl)benzenepentanamide (1.44 g.) in ethyl acetate-hydrogen chloride (3.4N, 30 ml.) was stirred for 30 minutes at room temperature, stripped of volatiles and triturated with ether, affording D,L-N-(3-methylbutyl)-benzenepentanamide as a gum in two crops (0.71 g., 500 mg.).

D. ZTyr(Bz)D-AlaHhfNHCH$_2$CH$_2$CHMe$_2$

By the method of part E of Example 1 (N-benzyloxycarbonyl-O-benzyl-L-tyrosyl)-D-alanyl hydrazide (part B of Example 1, 1.88 g.) was condensed with D,L-N-(3-methylbutyl)benzenepentanamide (1.1 g.) and the product was purified by precipitation as a gel from acetonitrile, affording D,L-2-[(N-benzyloxycarbonyl-O-benzyl-L-tyrosyl)-D-alanyl]amino-N-(3-methylbutyl)benzenepentanamide (2.40 g.).

E. HTyrD-AlaHhfNHCH$_2$CH$_2$CHMe$_2$

By the method of part F of Example 1 D,L-2-[(N-benzyloxycarbonyl-O-benzyl-L-tyrosyl)-D-alanyl]amino-N-(3-methylbutyl)benzenepentanamide (1.8 g.) was deprotected and purified (the eluant was 55:45 methanol-water containing 0.2% ammonium acetate). The product was lyophilized from dilute hydrochloride acid, affording as an amorphous white solid D,L-N-(3-methylbutyl)-2-[(L-tryosyl-D-alanyl)amino]benzenepentanamide monohydrochloride hemihydrate (60:40 mixture of diastereoisomers, 832 mg.), whose free base is the compound of Formula I wherein $R_1$, $R_2$, $R_3$, $R_5$ and $R_7$ are each hydrogen, $R_4$ is methyl, $R_6$ is $(CH_2)_mAr$ wherein m is 3 and Ar is phenyl, and $R_8$ is 3-methylbutyl.

EXAMPLE 8

A. 

By the method of part C of Example 1 S-2-(t-butoxycarbonylamino)benzenebutanoic acid (part A of Example 4, freed from 1.84 g. of the dicyclohexylamine salt) was condensed with methyl(3-methylbutyl)amine hydrochloride (551 mg.). An ethyl acetate-hexane solution of the product deposited crystals of an unidentified and unwanted material (70 mg.) which was separated. The filtrate was filtered through silica gel and stripped of volatiles. Trituration of the residue with hexane and removal of the hexane afforded S-2-(t-butoxycarbonylamino)-N-methyl-N-(3-methylbutyl)benzenebutanamide (1.43 g.).

B. 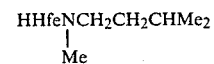

A solution of S-2-(t-butoxycarbonylamino)-N-methyl-N-(3-methylbutyl)benzenebutanamide (990 mg.) in ethyl acetate-hydrogen chloride (3.4N, 8 ml.) was stirred for one hour at room temperature. Addition of sufficient hexane to make the solution turbid failed to produce crystallization of the produce, so the mixture was stripped of volatiles, finally under high vacuum, affording S-2-amino-N-methyl-N-(3-methylbutyl)benzenebutanamide hydrochloride as a glass (800 mg.).

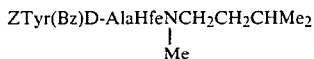
C.

By the method of part E of Example 1 (N-benzyloxycarbonyl-O-benzyl-L-tyrosyl)-D-alanyl hydrazide (part B of Example 1, 1.24 g.) was condensed with S-2-amino-N-methyl-N-(3-methylbutyl)benzenebutanamide hydrochloride (750 mg.) and the product was purified by high pressure liquid chromatography on silica gel using ethyl acetate-hexane (3:1) as the eluant, affording S-2-[(N-benzyloxycarbonyl-O-benzyl-L-tyrosyl)-D-alanyl]amino-N-methyl-N-(3-methylbutyl)-benzenebutanamide as a foam (1.4 g.).

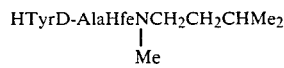
D.

By the method of part F of Example 1 S-2-[(N-benzyloxycarbonyl-O-benzyl-L-tyrosyl)-D-alanyl]amino-N-methyl-N-(3-methylbutyl)benzenebutanamide was deprotected and purified. The product crystallized from dilute hydrochloric acid (0.1N, 50 ml.) and was recrystallized from water, affording as a crystalline white solid (2S)-N-methyl-N-(3-methylbutyl)-2-[(L-tyrosyl-D-alanyl)amino]benzenebutanamide monohydrochloride (457 mg., m.r. 146°–151° C.), whose free base is the compound of Formula I wherein $R_1$, $R_2$, $R_3$, and $R_5$ are each hydrogen, $R_4$ and $R_7$ are each methyl, $R_6$ is $(CH_2)_m Ar$ wherein m is 2 and Ar is phenyl, and $R_8$ is 3-methylbutyl.

EXAMPLE 9

HTyrD-AlaHfeNH$_2$

A. BocHfeNH$_2$

By the method of part A of Example 1 using tetrahydrofuran instead of acetone as solvent S-2-(t-butoxycarbonylamino)benzenebutanoic acid (part A of Example 4, 3.9 g.) was condensed with concentrated aqueous ammonia (1.2 ml.) and the product was isolated by ethyl acetate extraction, affording S-2-(t-butoxycarbonylamino)benzenebutanamide as a crystalline solid (3.51 g., m.r. 147°–148° C.).

B. HHfeNH$_2$

A solution of S-2-(t-butoxycarbonylamino)benzenebutanamide (2.89 g.) in ethyl acetate-hydrogen chloride (3.4N, 20 ml.) was stirred at room temperature for one-half hour, then diluted with ethyl acetate (100 ml.), affording as a crystalline precipitate S-2-aminobenzenebutanamide hydrochloride (1.90 g., m.r. 250°–251° C.).

C. BocD-AlaHfeNH$_2$

By the method of part C of Example 1 using triethylamine instead of diisopropylethylamine N-(t-butoxycarbonyl)-D-alanine (1.6 g.) was condensed with S-2-aminobenzenebutamide (1.8 g.) and the product was crystallized from ethyl acetatehexane, affording S-2-[N-(t-butoxycarbonyl)-D-alanyl]aminobenzenebutanamide (1.81 g., m.r. 154°–155° C.).

D. HD-AlaHfeNH$_2$

A solution of S-2-[N-(t-butoxycarbonyl)-D-alanyl]aminobenzenebutanamide (1.75 g.) in ethyl acetate-hydrogen chloride (3.4N, 15 ml.) was stirred at room temperature for one-half hour, then diluted with ethyl acetate to a volume of 60 ml. Crystallization of the product from isopropyl alcohol afforded S-2-(D-alanyl)aminobenzenebutanamide hydrochloride (1.121 g., m.r. 227°–229° C. with decomposition).

E. ZTyr(Bz)D-AlaHfeNH$_2$

By the method of part A of Example 1 using tetrahydrofuran instead of acetone as solvent N-benzyloxycarbonyl-O-benzyl-L-tyrosine (1.014 g.) was condensed with S-2-(D-alanyl)aminobenzenebutanamide hydrochloride, affording S-2-[(N-benzyloxycarbonyl-O-benzyl-L-tyrosyl)-D-alanyl]aminobenzenebutanamide, part (1.038 g., m.r. 185°–192° C.) by crystallization from the reaction mixture and part (390 mg.) by ethyl acetate extraction of the residue obtained by concentrating the crystallization filtrate.

F. HTyrD-AlaHfeNH$_2$

By the method of part F of Example 1 S-2-[(N-benzyloxycarbonyl-O-benzyl-L-tyrosyl)-D-alanyl]aminobenzenebutanamide (955 mg.) was deprotected. The product was purified by reverse phase high pressure liquid chromatography using ammonium acetate (0.2%) in methanol-water (1:1) as the eluant and was isolated by lyophilization, first from dilute hydrochloric acid (0.1N) and then from water, affording as an amorphous white solid (2S)-2-[(L-tyrosyl-D-alanyl)amino]benzenebutanamide monohydrochloride monohydrate (208 mg.), whose free base is the compound of Formula I wherein $R_1$, $R_2$, $R_3$, $R_5$, $R_7$ and $R_8$ are each hydrogen, $R_4$ is methyl and $R_6$ is $(CH_2)_m Ar$ wherein m is 2 and Ar is phenyl.

EXAMPLE 10

MeTyrD-AlaHfeNH$_2$

A. ZMeTyr(Bz)OH

To a mixture of sodium hydride (50%, 9.64 g., prewashed with tetrahydrofuran to remove mineral oil) and tetrahydrofuran (120 ml.) were added dropwise with stirring first a filtered solution of N-benzyloxycarbonyl-O-benzyl-L-tyrosine (16.22 g.) in tetrahydrofuran (50 ml.), then methyl iodide (20 ml.), then tetrahydrofuran (10 ml.). The resulting mixture was stirred overnight at room temperature. Ethyl acetate (200 ml.) was added, then water (6 ml.) dropwise, and stirring was continued for one hour. Charcoal was added and the mixture was filtered. Water (70 ml.) and ether were added, affording a pale yellow solid which melted upon drying at 65° C. and resolidified upon cooling (15.72 g., m.r. 88°–90° C.). Recrystallization of the solid from ethyl acetate (12 ml., 5 ml. used for washing) afforded N-benzyloxycarbonyl-N-methyl-O-benzyl-L-tyrosine (14.13 g.; m.r. 90°–91.5° C.).

B. ZMeTyr(Bz)D-AlaHfeNH₂

By the method of part C of Example 1 using triethylamine instead of diisopropylethylamine N-benzyloxycarbonyl-N-methyl-O-benzyl-L-tyrosine (1.05 g.) was condensed with S-2-(D-alanyl)aminobenzenebutanamide (free base of product of part D of Example 9, 755 mg.), affording S-2-[(N-benzyloxycarbonyl-N-methyl-O-benzyl-L-tyrosyl)-D-alanyl]aminobenzenebutanamide (1.15 g.).

C. MeTyrD-AlaHfeNH₂

By the method of part F of Example 1 S-2-[(N-benzyloxycarbonyl-N-methyl-O-benzyl-L-tyrosyl)-D-alanyl]aminobenzenebutanamide (1.1 g.) was deprotected and purified. The product was chromatographed twice, first using ammonium acetate (0.2%), first in methanol-water (50:50), and then using methanol-water (40:60), as the eluant and was isolated by lyophilization as an amorphous white solid (2S)-2-[(N-methyl-L-tyrosyl-D-alanyl)amino]benzenebutanamide monohydrochloride monohydrate (215 mg.), whose free base is the compound of Formula I wherein $R_2$, $R_3$, $R_5$, $R_7$ and $R_8$ are each hydrogen, $R_1$ and $R_4$ are each methyl and $R_6$ is $(CH_2)_mAr$ wherein m is 2 and Ar is phenyl.

EXAMPLE 11

HTyrD-AlaHfeNHMe

A. BocHfeNHMe

By the method of part A of Example 1 using tetrahydrofuran instead of acetone as solvent S-2-(t-butoxycarbonylamino)benzenebutanoic acid (part A of Example 4, 2.936 g.) was condensed with methylamine (3.4N in tetrahydrofuran, 3.1 ml.) and the product was isolated by ethyl acetate extraction, affording S-2-(t-butoxycarbonylamino)-N-methylbenzenebutanamide as a solid (3.275 g.).

B. HHfeNHMe

A solution of S-2-(t-butoxycarbonylamino)-N-methylbenzenebutanamide (2.98 g.) in ethyl acetate-hydrogen chloride (3.4N, 30 ml.) was stirred at room temperature, then diluted with ethyl acetate to a volume of about 75 ml., affording as a crystalline precipitate S-2-amino-N-methylbenzenebutanamide hydrochloride (1.76 g., m.r. 200°–202° C.).

C. BocD-AlaHfeNHMe

By the method of part A of Example 1 using tetrahydrofuran instead of acetone as solvent N-(t-butoxycarbonyl)-D-alanine (1.3 g.) was condensed with S-2-amino-N-methylbenzenebutanamide hydrochloride (1.6 g.), affording S-2-[N-(t-butoxycarbonyl)-D-alanyl]amino-N-methylbenzenebutanamide, part (1.360 g., m.r. 163°–165° C.) by crystallization from ethyl acetate and part (1.186 g.) by extractive isolation from the crystallization filtrate.

D. HD-AlaHfeNHMe

A mixture of S-2-[N-(t-butoxycarbonyl)-D-alanyl]amino-N-methylbenzenebutanamide (1.60 g.) in ethyl acetate-hydrogen chloride (3.4N, 15 ml.) was stirred for ¾ hour at room temperature, then diluted with ether (35 ml.). The supernatant liquid was decanted. Since TLC suggested that the residue contained unchanged starting material, it was dissolved in acetic acid saturated with hydrogen chloride (15 ml.). The solution was stirred for one and one half hours at room temperature, then stripped of volatiles. The residue was subjected to high vacuum (0.1 mm.) for two hours, affording S-2-(D-alanyl)amino-N-methylbenzenebutanamide (1.61 g.).

E. ZTyr(Bz)D-AlaHfeNHMe

By the method of part A of Example 1 using tetrahydrofuran instead of acetone as solvent N-benzyloxycarbonyl-O-benzyl-L-tyrosine (810 mg.) was condensed with S-2-(D-alanyl)amino-N-methylbenzenebutanamide (600 mg.), affording S-2-[(N-benzyloxycarbonyl-O-benzyl-L-tyrosyl)-D-alanyl]amino-N-methylbenzenebutanamide, part (787 mg., m.r. 227°–229° C.) by crystallization from the reaction solution and part (120 mg., m.r. 208°–212° C.) by ethyl acetate extraction of the residue obtained by concentrating the crystallization filtrate.

F. HTyrD-AlaHfeNHMe

By the method of part F of Example 1 S-2-[(N-benzyloxycarbonyl-O-benzyl-L-tyrosyl)-D-alanyl]amino-N-methylbenzenebutanamide (889 mg.) was deprotected and purified. The eluant was ammonium acetate (0.2%) in methanol-water (1:1). The product was isolated by lyophilization from dilute hydrochloric acid (0.1N), affording as an amorphous white solid (2S)-N-methyl-2-[(L-tyrosyl-D-alanyl)amino]benzenebutanamide monohydrochloride monohydrate (379 mg.), whose free base is the compound of Formula I wherein $R_1$, $R_2$, $R_3$, $R_5$ and $R_7$ are each hydrogen, $R_4$ and $R_8$ are each methyl and $R_6$ is $(CH_2)_mAr$ wherein m is 2 and Ar is phenyl.

EXAMPLE 12

HTyrD-AlaMeHfeNHCH₂CH₂CHMe₂

A. BocMeHfeOH

A solution of S-2-(t-butoxycarbonylamino)benzenebutanoic acid (4.485 g.) in tetrahydrofuran (50 ml.) was added dropwise at room temperature during 30 minutes to a suspension of sodium hydride (50% dispersion in mineral oil, 2.32 g.) in tetrahydrofuran (100 ml.). Stirring was continued for one and one half hours at 25° C. Methyl iodide (25 g.) was added and the mixture was stirred at room temperature for 48–50 hours, then diluted with water (100 ml.) and concentrated to 80–100 ml. in volume. Aqueous sodium hydroxide (1N, 20 ml.) was added. The mixture was washed twice with hexane (100 ml. each time), acidified to pH 3 with solid citric acid and extracted three times with ethyl acetate. The combined ethyl acetate extracts were washed three times with water and twice with saturated aqueous sodium chloride, dried over magnesium sulfate and stripped of ethyl acetate. The residue was mixed with ether, which was evaporated, then dried under high vacuum, affording as a white solid S-2-(methyl-t-butoxycarbonylamino)benzenebutanoic acid (4.698 g.).

B. BocMeHfeNHCH₂CH₂CHMe₂

By the method of part A of Example 1 using tetrahydrofuran instead of acetone as solvent and N-methylmorpholine instead of triethylamine as base S-2-(methyl-t-butoxycarbonylamino)benzenebutanoic acid (2.20 g.) was condensed with 3-methylbutylamine (655 mg.) and the product was isolated by ethyl acetate extraction, affording as a viscous syrup S-2-(methyl-t-butoxycarbonylamino)-N-(3-methylbutyl)benzenebutanamide (2.716 g.).

C. MeHfeNHCH$_2$CH$_2$CHMe

A solution of S-2-(methyl-t-butoxycarbonylamino)-N-(3-methylbutyl)benzenebutanamide (2.54 g.) in dioxane-hydrogen chloride (3.9N, 50 ml.) was stirred for one and one half hours at room temperature, then concentrated. The residue was triturated with ether, stripped of ether and dried under high vacuum, affording as a white solid S-2-methylamino-N-(3-methylbutyl)benzenebutanamide hydrochloride (2.15 g.).

D. BocTyr(tBu)D-AlaMeHfeNHCH$_2$CH$_2$CHMe$_2$

A solution of dicyclohexylcarbodiimide (716 mg.) in methylene dichloride (10 ml.) was added with stirring to a −5° to −10° C. solution of N-(t-butoxycarbonyl)-O-(t-butyl)-L-tyrosyl-D-alanine (1.390 g.), S-2-methylamino-N-(3-methylbutyl)benzenebutanamide hydrochloride (1.00 g.), 1-hydroxybenzotriazole (862 mg.) and triethylamine (345 mg.) in methylene dichloride (50 ml.). Stirring was continued at −5° C. for two hours, then at 0° C. for two hours, then at room temperature overnight. The mixture was diluted with methylene dichloride to a volume of about 100 ml., filtered and stripped of volatiles. A solution of the residue in ethyl acetate (300 ml.) was washed with water, aqueous citric acid (1N), saturated aqueous sodium bicarbonate and saturated aqueous sodium chloride, dried, and stripped of ethyl acetate. High pressure liquid chromatography of the residue (1.56 g.) on silica gel using ether-hexane (90:10) as the eluant afforded S-2-methyl-[N-(t-butoxycarbonyl-O-(t-butyl)-L-tyrosyl-D-alanyl-]amino-N-(3-methylbutyl)benzenebutanamide as a white foam (0.600 g.) and in two other slightly impure fractions (392 mg., 107 mg.).

E. HTyrD-AlaMeHfeNHCH$_2$CH$_2$CHMe$_2$

A solution of S-2-methyl[N-(t-butoxycarbonyl)-O-(t-butyl)-L-tyrosyl-D-alanyl]amino-N-(3-methylbutyl)-benzenebutanamide (550 mg.) in dioxane-hydrogen chloride (3.9N, 50 ml.) was stirred for one and one half hours at room temperature, stripped of volatiles and reevaporated twice from methanol and twice from ether. Attempted purification of the residue (584 mg.) by reverse phase high pressure liquid chromatography on octadecylsilated silica gel using methanol-water (65:35) containing ammonium acetate (0.2%) was unsuccessful. Part (220 mg.) of the twice-lyophilized chromatographic product (278 mg.) was purified by column chromatography using ethyl acetate-(pyridine-acetic acid-water, 55:20:25) (3:1) as the eluant (500 drops per fraction). Fractions 21–29 contained the product (178 mg.), which was lyophilized first from dilute hydrochloric acid and then from water, affording as an amorphous white solid (2S)-N-(3-methylbutyl)-2-[methyl(L-tyrosyl-D-alanyl)amino]benzenebutanamide monohydrochloride dihydrate (147 mg.), whose free base is the compound of Formula I wherein R$_1$, R$_2$, R$_3$ and R$_7$ are each hydrogen, R$_4$ and R$_5$, R$_6$ is (CH$_2$)$_m$Ar wherein m is 2 and Ar is phenyl and R$_8$ is 3-methylbutyl.

EXAMPLE 13

MeTyrD-AlaHfeNHMe

A. ZMeTyr(Bz)D-AlaHfeNHMe

By the method of part C of Example 1 N-benzyloxycarbonyl-N-methyl-O-benzyl-L-tyrosine (part A of Example 10, 839 mg.) was condensed with S-2-(D-alanyl)amino-N-methylbenzenebutanamide (part D of Example 11, 600 mg.) and the product was purified by high pressure liquid chromatography on silica gel using ethyl acetate as the eluant, affording S-2-[(N-benzyloxycarbonyl-N-methyl-O-benzyl-L-tyrosyl)-D-alanylamino]-N-methylbenzenebutanamide as a gum (885 mg.).

B. MeTyrD-AlaHfeNHMe

By the method of part F of Example 1 S-2-[(N-benzyloxycarbonyl-N-methyl-O-benzyl-L-tyrosyl)-D-alanylamino]-N-methylbenzenebutanamide (863 mg.) was deprotected and purified (the eluant was 45:55 methanol-water containing 0.2% ammonium acetate). The product was lyophilized, first from dilute hydrochloric acid (0.1N) and then from water, affording as an amorphous white solid (2S)-N-methyl-2-[(N-methyl-L-tyrosyl-D-alanyl)amino]benzenebutanamide monohydrochloride dihydrate (227 mg.), whose free base is the compound of Formula I wherein R$_1$, R$_4$ and R$_8$ are each methyl, R$_2$, R$_3$, R$_5$ and R$_7$ are each hydrogen, and R$_6$ is (CH$_2$)$_m$Ar wherein m is 2 and Ar is phenyl.

EXAMPLE 14

HTyrD-AlaHfeNHCH$_2$CH$_2$NMe

A. BocHfeNHCH$_2$CH$_2$NMe$_2$

A solution of S-2-(t-butoxycarbonylamino)benzenebutanoic acid pentafluorophenyl ester (2.0 g.) and N,N-dimethylethylenediamine (0.5 ml.) in tetrahydrofuran was stirred for three hours at room temperature. The crude product was isolated by ethyl acetate extraction and purified by reverse phase high pressure liquid chromatography on octadecylsilated silica gel using methanol-water (70:30) containing 0.2% ammonium acetate as the eluant, affording S-2-(t-butoxycarbonylamino)-N-(2-dimethylaminoethyl)benzenebutanamide as a light yellow gum (780 mg.).

B. HHfeNHCH$_2$CH$_2$NMe$_2$

A solution of S-2-(t-butoxycarbonylamino)-N-(2-dimethylaminoethyl)benzenebutanamide (690–700 mg.) in ethyl acetate-hydrogen chloride (3.9N, 30 ml.) was stirred for two hours at room temperature, then stripped of volatiles, affording S-2-amino-N-(2-dimethylaminoethyl)benzenebutanamide dihydrochloride.

C. ZTyr(Bz)D-AlaHfeNH(CH$_2$)$_2$NMe$_2$

By the method of part E of Example 1 (N-benzyloxycarbonyl-O-benzyl-L-tyrosyl)-D-alanyl hydrazide (part B of Example 1, 971 mg.) was condensed with the entire product of part B of this example. The reaction mixture was quenched in water (100 ml.) containing saturated aqueous sodium bicarbonate (20 ml.) and the crystalline precipitate was recrystallized from methanol, affording S-2-[(N-benzyloxycarbonyl-O-benzyl-L-tyrosyl)-D-alanyl]amino-N-(2-dimethylaminoethyl)-benzenebutanamide (690 mg.).

D. HTyrD-AlaHfeNHCH$_2$CH$_2$NMe$_2$

By the method of part F of Example 1 S-2-[(N-benzyloxycarbonyl-O-benzyl-L-tyrosyl)-D-alanyl]amino-N-(2-dimethylaminoethyl)benzenebutanamide (720 mg.) was deprotected and purified (the eluant was 55:45 methanol-water containing 0.2% ammonium acetate). The product was lyophilized, first from dilute hydrochloric acid and then from water, affording as an amorphous white solid (2S)-N-[(2-dimethylamino)ethyl]-2-[(L-tyrosyl-D-alanyl)amino]benzenebutanamide dihydrochloride hydrate (5:2), whose free base is the compound of Formula I wherein $R_1$, $R_2$, $R_3$, $R_5$ and $R_7$ are each hydrogen, $R_4$ is methyl, $R_6$ is $(CH_2)_m Ar$ wherein m is 2 and Ar is phenyl, and $R_8$ is $(CH_2)_n X$ wherein n is 2 and X is dimethylamino.

EXAMPLE 15

HTyrD-MetHfeNHCH$_2$CH$_2$CHMe$_2$

A. BocD-MetHfeNHCH$_2$CH$_2$CHMe$_2$

By the method of part A of Example 1 using tetrahydrofuran instead of acetone as solvent and N-methylmorpholine instead of triethylamine as base N-(t-butoxycarbonyl)-D-methionine (2.285 g.) was condensed with S-2-amino-N-(3-methylbutyl)benzenebutanamide hydrochloride (2.71 g.) and the product (4.320 g.) was purified by high pressure liquid chromatography on silica gel using hexane-ethyl acetate (56:44) as the eluant, affording S-2-[N-(t-butoxycarbonyl)-D-methionyl]amino-N-(3-methylbutyl)benzenebutanamide as a crystalline white solid (3.222 g., m.r. 133°–135° C.).

B. HD-MetHfeNHCH$_2$CH$_2$CHMe$_2$

A solution of S-2-[N-(t-butoxycarbonyl)-D-methionyl]amino-N-(3-methylbutyl)benzenebutanamide (3.08 g.) in ethyl acetate-hydrogen chloride (3.9N, 50 ml.) was stirred for one hour at room temperature, then stripped fo volatiles. The residue was evaporated twice more from ethyl acetate, triturated with ether and dried, affording S-2-(D-methionyl)amino-N-(3-methylbutyl)benzenebutanamide as a white solid (2.646 g.).

C. BocTyr(tBu)D-MetHfeNHCH$_2$CH$_2$CHMe$_2$

By the method of part C of Example 1 using N-methylmorpholine instead of diisopropylethylamine as base and dimethylformamide as cosolvent, N-(t-butoxycarbonyl)-O-(t-butyl)-L-tyrosine (2.130 g.) was condensed with S-2-(D-methionyl)amino-N-(3-methylbutyl)benzenebutanamide (2.622 g.) and the product (4.158 g.) was purified by high pressure liquid chromatography on silica gel using ethanol (2.5%) in methylene dichloride as the eluant, affording S-2-[N-(t-butoxycarbonyl)-O-(t-butyl)-L-tyrosyl-D-methionyl]amino-N-(3-methylbutyl)benzenebutanamide as a white solid (3.75 g.).

D. HTyrD-MetHfeNHCH$_2$CH$_2$CHMe$_2$

A solution of S-2-[N-(t-butoxycarbonyl)-O-(t-butyl)-L-tyrosyl-D-methionyl]amino-N-(3-methylbutyl)benzenebutanamide in ethyl acetate-hydrogen chloride (3.9N, 60 ml.) was stirred for one half hour at room temperature and stripped of volatiles. The residue was evaporated twice more from ethyl acetate and dissolved in water (150 ml.). The solution was filtered to remove unchanged starting material (220 mg.; this was similarly deprotected to give 215 mg. of product) and was lyophilized in two portions, affording as an amorphous white solid (2S)-N-(3-methylbutyl)-2-[(L-tyrosyl-D-methionyl)amino]benzenebutanamide monohydrochloride sesquihydrate (1.320 g., 1.225 g.), whose free base is the compound of Formula I wherein $R_1$, $R_5$ and $R_7$ are each hydrogen, the

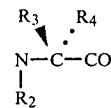

moiety is D-methionyl, $R_6$ is $(CH_2)_m Ar$ wherein m is 2 and Ar is phenyl and $R_8$ is 3-methylbutyl.

EXAMPLE 16

HTyrD-Met(O)HfeNHCH$_2$CH$_2$CHMe$_2$

Hydrogen peroxide (3%, 2.70 ml.) was added to a solution of (2S)-N-(3-methylbutyl)-2-[(L-tyrosyl-D-methionyl)amino]benzenebutanamide monohydrochloride sesquihydrate (1.225 g.) in acetic acid (25 ml.). The solution was stirred for two hours at room temperature, then stripped of volatiles. A solution of the residue in water (50 ml.) was filtered and lyophilized, affording as an amorphous white solid (2S)-N-(3-methylbutyl)-2-[(L-tyrosyl-D-methionyl)amino]benzenebutanamide S-oxide monohydrochloride sesquihydrate, whose free base is the compound of Formula I wherein $R_1$, $R_5$ and $R_7$ are each hydrogen, the

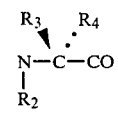

moiety is D-S-oxomethionyl, $R_6$ is $(CH_2)_m Ar$ wherein m is 2 and Ar is phenyl and $R_8$ is 3-methylbutyl.

EXAMPLE 17

HTyrD-Met(O$_2$)HfeNHCH$_2$CH$_2$CHMe$_2$

Hydrogen peroxide (3%, 1.10 ml.) was added to a solution of (2S)-N-(3-methylbutyl)-2-[(L-tyrosyl-D-methionyl)amino]benzenebutanamide monohydrochloride sesquihydrate (215 mg.) in acetic acid (6 ml.). After the solution had been stirred for three hours at room temperature TLC showed only sulfoxide. More hydrogen peroxide (30%, 1.10 ml.) was added and stirring was continued for 20 hours. The solution was stripped of volatiles. Since TLC and HPLC showed that the product (205 mg.) after lyophilization contained about 15% impurity, it (198 mg.) was purified by column chromatography on silica gel (80 g.) using 3:1 ethyl acetate-(pyridine-acetic acid-water) (11:4:5) as eluant. The product was isolated by lyophilization, first from dilute hydrochloric acid (0.1N, 50 ml.) and then from water (30 ml.), affording (2S)-N-(3-methylbutyl)-2-[(L-tyrosyl-D-methionyl)amino]benzenebutanamide S,S-dioxide monohydrochloride hydrate (2:5) (126 mg.), whose free base is the compound of Formula I wherein $R_1$, $R_5$ and $R_7$ are each hydrogen, the

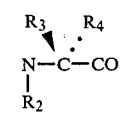

moiety is D-S-dioxomethionyl, $R_6$ is $(CH_2)_m Ar$ wherein m is 2 and Ar is phenyl and $R_8$ is 3-methylbutyl.

EXAMPLE 18

HTyrD-AlaHfeNHCH₂CH₂Ph

A. BocHfeNHCH₂CH₂Ph

By the method of part A of Example 1 using tetrahydrofuran instead of acetone as solvent S-2-(t-butoxycarbonylamino)benzenebutanoic acid (part A of Example 4, freed from 9.4 g. of the dicyclohexylamine salt) was condensed with 2-phenylethylamine (2.42 g.). The product (7.46 g.) was recrystallized from ethyl acetate, affording S-2-(t-butoxycarbonylamino)-N-(2-phenylethyl)benzenebutanamide (4.212 g., m.r. 122°–123° C.).

B. HHfeNHCH₂CH₂Ph

A solution of S-2-(t-butoxycarbonylamino)-N-(2-phenylethyl)benzenebutanamide (4.1 g.) in ethyl acetate-hydrogen chloride (3.9N, 20 ml.) was stirred for one hour at room temperature, then stripped of volatiles. A solution of the residue in isopropyl alcohol and ether was filtered to remove a small amount (123 mg.) of crystalline impurity, then stripped of solvents, affording S-2-amino-N-(2-phenylethyl)benzenebutanamide as a syrup (3.23 g.).

C. ZTyr(Bz)D-AlaHfeNHCH₂CH₂Ph

By the method of part E of Example 1 N-benzyloxycarbonyl-O-benzyl-L-tyrosyl)-D-alanyl hydrazide (part B of Example 1, 4.91 g.) was condensed with S-2-amino-N-(2-phenylethyl)benzenebutanamide (3.09 g.). The ethyl acetate-soluble part of the product (7.52 g.) was recrystallized from acetonitrile, affording S-2-[(N-benzyloxycarbonyl-O-benzyl-L-tyrosyl)-D-alanyl-]amino-N-(2-phenylethyl)benzenebutanamide (4.159 g., m.r. 202°–206° C.).

D. HTyrD-AlaHfeNHCH₂CH₂Ph

By the method of part F of Example 1 S-2-[(N-benzyloxycarbonyl-O-benzyl-L-tyrosyl)-D-alanyl]amino-N-(2-phenylethyl)benzenebutanamide (3.71 g.) was deprotected. The product was purified by recrystallization from isopropyl alcohol as the acetate salt (1.56 g., m.r. 161°–163° C.), which was converted into the phosphate salt by ion exchange and lyophilized, affording as an amorphous white solid (2S)-N-(2-phenylethyl)-2-[(L-tyrosyl-D-alanyl)amino]benzenebutanamide phosphate (1:1) salt sesquihydrate (848 mg.), whose free base is the compound of Formula I wherein $R_1$, $R_2$, $R_3$, $R_5$ and $R_8$ are each hydrogen, $R_4$ is methyl, and $R_6$ and $R_7$ are each $(CH_2)_m Ar$ wherein m is 2 and Ar is phenyl.

BIOLOGICAL PROPERTIES OF THE COMPOUNDS

As stated above the compounds of Formula I and Examples 1–3 are useful as analgesics and/or opiate antagonists. These utilities are shown in the guinea pig ileum test.

Guinea Pig Ileum Test

Adult male guinea pigs (Charles River, Hartley strain) weighing 300–500 g. are decapitated, and the terminal ileum is exposed by reflecting the overlying cecum, severed at the ileocecal juncture, and removed while cutting the mesenteric attachments to avoid excessive traction on the tissue. The ileum (about 30 cm. in length) is transferred to a beaker containing warm modified Krebs-Henseleit solution (118 mM sodium chloride, 4.75 mM potassium chloride, 2.54 mM calcium chloride, 1.19 mM potassium dihydrogen phosphate, 1.2 mM magnesium sulfate, 25 mM sodium bicarbonate, 11 mM glucose, 20 μM choline chloride and 0.125 μM pyrilamine maleate). The terminal (aboral) portion (about 10 cm, in length) is discarded, and segments (3–4 cm. in length) are cut from the remainder and gently slid onto a glass rod (5–6 mm. in diameter) and arranged so that the mesenteric attachment is in a straight line. A cotton swab moistened in the solution is then carefully used to separate the longitudinal muscle from the underlying circular muscle. The longitudinal muscle and adhering myenteric plexus is then gently removed from the remaining tissue with forceps.

Strips of thus prepared longitudinal muscle are mounted in a double-jacketed organ bath (5 ml.) under tension (1.0 g.), connected to isometric transducers (Grass FT 0.03), bathed in the modified Krebs-Henseleit solution described above, aerated with oxygen-carbon dioxide (95:5) and maintained at 37° C.

Stimulators (Grass S-44) are set to deliver repetitive, monophasic square wave field stimulation (supramaximal voltage, 0.10 Hz., 0.25 msec. duration) through platinum ring electrodes at the top and bottom of the bath. Regular contractions of the muscle, which result from electrically-induced liberation of acetylcholine from postganglionic parasympathetic nerves, are recorded on a polygraph (Grass model 5). Following tissue equilibration (45–60 min.) and repeated washing (every 10 min.) an aqueous solution of a reference or test compound is added to the bath in a microliter volume (1.25–250 μl) and reductions in muscle twitch height are recorded. More compound can be added with (single dose method) or without (cumulative dose method) first washing the preparation.

From the results a half-maximal inhibitory concentration (IC50) value for the compound is computed by regression analysis of a linear plot of logarithm of concentration against percent of inhibition of twitch height (probits). The ratio of the IC50 value of a reference compound to that of a test compound tested in the same preparation is the molar potency ratio. At least four preparations are tested simultaneously (N=4), and the resulting molar potency ratios are averaged.

The following results were obtained using the examples as test compounds and Met[5]-enkephalin as the reference compound:

| Compound | Average Molar Potency Ratio |
| --- | --- |
| Met[5]-enkephalin | 100 |
| Example 1 | 25 |
| Example 2 | 6 |
| Example 3 | 5 |
| Example 4 | 430 |
| Example 5 | 12 |
| Example 6 | 280 |
| Example 7 | 5 |
| Example 8 | 45 |
| Example 9 | 120 |
| Example 10 | 94 |
| Example 11 | 190 |
| Example 12 | 10 |
| Example 13 | 59 |
| Example 14 | 41 |
| Example 15 | 515 |
| Example 16 | 1200 |
| Example 17 | 110 |
| Example 18 | 240 |

Quantitation of the antagonist potency of a pure, competitive antagonist on a given receptor population involves determination of the pA2, which is the negative log of the molar concentration of antagonist that shifts the agonist dose response curve by a factor of two. Measurement of the antagonist potency of compounds having both agonist and antagonist properties is accomplished by calculating the equilibrium dissociation constant, Ke(nM). Ke and pA2 are related by the equation pA2 = −log Ke if the compound is an antagonist having no agonist activity.

To carry out the pharmaceutical composition aspect of the invention the compounds of Formula I can be prepared for oral or parenteral administration in liquid or solid dosage form as solutions, suspensions, emulsions, capsules or tablets with conventional pharmaceutical vehicles and adjuncts by conventional pharmaceutical techniques.

I claim:

1. HTyrD-DaaPheNHCH$_2$CH$_2$CHMe$_2$ or a pharmaceutically acceptable acid addition salt thereof.

* * * * *